US007118216B2

(12) United States Patent
Roorda

(10) Patent No.: US 7,118,216 B2
(45) Date of Patent: *Oct. 10, 2006

(54) METHOD AND APPARATUS FOR USING ADAPTIVE OPTICS IN A SCANNING LASER OPHTHALMOSCOPE

(75) Inventor: Austin Roorda, Houston, TX (US)

(73) Assignee: University of Rochester, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/125,331

(22) Filed: May 10, 2005

(65) Prior Publication Data

US 2006/0087617 A1 Apr. 27, 2006

Related U.S. Application Data

(63) Continuation of application No. 10/231,491, filed on Aug. 30, 2002, now Pat. No. 6,890,076.

(60) Provisional application No. 60/316,173, filed on Aug. 30, 2001.

(51) Int. Cl.
*A61B 3/00* (2006.01)
*A61B 3/10* (2006.01)
*G02B 26/08* (2006.01)

(52) U.S. Cl. .................. 351/205; 351/221; 351/246; 359/202

(58) Field of Classification Search ................ 351/200, 351/205, 206, 211–216, 220, 221, 246, 247; 348/195, 202, 203, 205; 359/196, 197, 201, 359/202, 298; 600/558; 128/898

See application file for complete search history.

(56) References Cited

U.S. PATENT DOCUMENTS

| 4,579,430 A | 4/1986 | Bille |
| 4,795,256 A | 1/1989 | Krause et al. |
| 4,856,891 A | 8/1989 | Pflibsen et al. |
| 5,049,740 A | 9/1991 | Pines et al. |
| 5,777,719 A | 7/1998 | Williams et al. |
| 5,895,422 A | 4/1999 | Hauber |
| 6,299,311 B1 | 10/2001 | Williams et al. |
| 6,331,059 B1 | 12/2001 | Kudryashov et al. |
| 6,361,170 B1 | 3/2002 | Bille |
| 6,550,917 B1 | 4/2003 | Neal et al. |
| 6,554,775 B1 | 4/2003 | Peyman et al. |
| 6,588,900 B1 | 7/2003 | Le Gargasson et al. |
| 6,609,794 B1 | 8/2003 | Levine |
| 2002/0154398 A1 | 10/2002 | Wolleschensky et al. |

FOREIGN PATENT DOCUMENTS

WO WO 00/59368 10/2000

OTHER PUBLICATIONS

A. Roorda, et al., "Adaptive Optics Scanning Laser Ophthalmoscopy", Optics Express, vol. 10, No. 9, May 6, 2002, pp. 405-412.

*Primary Examiner*—Charles A Marmor, II
*Assistant Examiner*—John R Sanders
(74) *Attorney, Agent, or Firm*—Blank Rome LLP

(57) ABSTRACT

A scanning laser ophthalmoscope incorporates adaptive optics to compensate for wavefront aberrations in the eye. Light from a light source is scanned onto the retina. Light reflected from the retina is detected for imaging and is also used for wavefront sensing. The sensed wavefront aberrations are used to control an adaptive optic device, such as a deformable mirror, disposed in the path of the light from the source in order to compensate for the aberrations.

30 Claims, 9 Drawing Sheets

METHOD AND APPARATUS FOR USING ADAPTIVE OPTICS IN A SCANNING LASER OPHTHALMOSCOPE

This application is a Continuation of application Ser. No. 10/231,491 filed on Aug. 30, 2002 now U.S. Pat. No. 6,890,076, which claims the benefit of Provisional Application No. 60/316,173, filed Aug. 30, 2001.

REFERENCE TO RELATED APPLICATION

The present application claims the benefit of U.S. Provisional Application No. 60/316,173, filed Aug. 30, 2001, whose disclosure is hereby incorporated by reference in its entirety into the present disclosure.

STATEMENT OF GOVERNMENT INTEREST

The present invention was developed under NIH Grant No. R1 EY 13299-01 and NSF Grant No. AST 9876783. The government has certain rights in the invention.

FIELD OF THE INVENTION

The present invention is directed to scanning laser ophthalmoscopes (SLO) and methods of using them, and more particularly to such ophthalmoscopes and methods of using them which involve the use of adaptive optics (AO) to compensate for wavefront aberrations in the eye under examination.

DESCRIPTION OF RELATED ART

The development of ocular imaging has progressed since the first scanning laser ophthalmoscope (SLO) was disclosed in U.S. Pat. No. 4,213,678. The first patent relating to imaging the ocular fundus while correcting for eye aberrations was Bille's patent titled, "Method and Apparatus for forming an image of the ocular fundus" (U.S. Pat. No. 4,579,430). A scanning laser ophthalmoscope for high lateral-resolution imaging was developed which was capable of imaging a living human eye but did not use adaptive optics (AO) and had limited resolution at the microscopic level.

The first published report of using AO in a SLO was by Dreher et al, "Active optical depth resolution improvement of the laser tomographic scanner," *App. Opt.* 28, 804–808 (1989), to improve the axial resolution of their instrument. The authors of that article did not use a wavefront sensor to measure the aberrations of the eye, and their wavefront corrector was used only to compensate for the astigmatism of the eye. Similarly, the axial resolution of a SLO has been improved by using a rigid contact lens to eliminate the aberrations of the cornea, and modest improvements in a fundus image has been obtained with a fundus camera equipped with a membrane deformable mirror. Liang et al, "Supernormal vision and high-resolution retinal imaging through adaptive optics," *J. Opt. Soc. Am. A* 14, 2884–2892 (1997), used an ophthalmoscope equipped with AO to image microscopic structures in the retina, but they did not apply the technology to a SLO.

In U.S. Pat. No. 6,095,651, a Hartmann-Shack wavefront sensor and wavefront compensation device are used to measure the high-order aberrations of the eye. A Hartmann-Shack wavefront sensor was also used by Bille in U.S. Pat. No. 6,155,684 to measure aberrations for wavefront compensation as a means to improve vision. A modified Hartmann-Shack wavefront sensor is described by Williams et al. in U.S. Pat. No. 6,199,986, wherein a method for real time measurement of the aberrations of the eye is described.

Therapeutic applications of SLOs with AO include microphotocoagulation and photodynamic therapy. In U.S. Pat. No. 6,186,628, Van de Velde describes the use of a scanning laser ophthalmoscope with an adaptive element for microphotocoagulation and photodynamic therapy. The wavefront sensing technique, described in another patent, entitled "Scanning laser ophthalmoscope for retinal microphotocoagulation and measurement of wavefront aberrations" (U.S. Pat. No. 5,943,117) employs a SLO to measure the wavefront aberrations of the eye. This technique is not used widely.

Although there are a number of patents covering SLO's, they do not propose a method for wavefront sensing whereby the light path is scanned/descanned using the same optics and light source as that used for imaging the ocular fundus. Methods that do not use the same optics for wavefront sensing and light detection are subject to a common phenomena called "non-common path errors," where the aberrations on the path to the wavefront sensor are different than those reaching the light detector for imaging.

By implementing AO to measure and correct high-order aberrations in an areal imaging system, such as a CCD camera or a film camera, the quality of retinal images will be improved. However, areal imaging techniques are limited in that they cannot suppress light from layers in front of or behind the focal plane of the ophthalmoscope. Because of this limitation, the images may have high resolution, but will suffer from low contrast because of scattered light from structures outside of the best focal plane.

To date, there has been no successful application of AO into a SLO. The one previous design published by Dreher et al. did not include wavefront sensing in the measurement. The benefits of AO cannot be realized without wavefront sensing being an integral part of the system. Bille's above-cited patent describes a design for a SLO that integrates a wavefront sensor into the design, but it does not use the same path as the light detection path and is therefore subject to the problem of non-common path errors.

SUMMARY OF THE INVENTION

It will be apparent from the above that a need exists in the art to integrate adaptive optics into retinal imaging. It is therefore an object of the invention to provide a scanning laser ophthalmoscope with adaptive optics.

It is another object of the invention to do so while avoiding non-common path errors.

It is a further object of the invention to provide axial sectioning in a scanning laser ophthalmoscope.

To achieve the above and other objects, the present invention is directed to a system and method whereby AO can be efficiently and effectively implemented in a scanning laser ophthalmoscope. The present invention will be an improvement on instruments used to take microscopic images of the retina in living human eyes and will have improved optical sectioning capability over currently available SLO's.

The present invention's implementation of AO is efficient because it uses the same optical path as the SLO. The present invention's implementation is effective because it is designed to optimize image quality, both axially and laterally, over the entire field of view of the ophthalmoscope.

The SLO is a device used to take images of the retina of a living human eye. In the SLO, scattered light is measured from a focused spot of light as it is scanned across the retina in a raster pattern. The image is built over time, pixel by pixel, as the spot moves across the retina. An aperture conjugate to (in the image plane of) the desired focal plane in the retina and prior to the light detector can be used to reduce scattered light originating from planes other than the plane of focus. The confocal aperture can be used to do optical slicing, or imaging of different layers in the human retina.

AO describes a set of techniques to measure and compensate for aberrations, or optical defects, in optical systems. AO, when applied to the optical system of the eye, can provide substantial improvements in the sharpness of retinal images that are normally degraded from the aberrations. Implementation of AO requires the use of a wavefront sensor, which is a device to measure the aberrations of the optical system, and a wavefront corrector, which is a device used to compensate for the aberrations in an optical system.

In one particular embodiment, the adaptive optics scanning laser ophthalmoscope wavefront sensing, wavefront compensation and raster scanning.

(i) Light delivery: Light delivery can be from a plurality of laser sources of different wavelengths, depending on the application. Light is relayed through the instrument via mirrors, which do not suffer from chromatic aberration. Furthermore, unlike lenses, mirrors do not produce back reflections that can enter into the light detection arm.

(ii) Light detection: Light is detected with a detector such as a very sensitive light detector and amplifier; in a preferred embodiment, a photomultiplier tube is used. Prior to the light detector in the preferred embodiment is the confocal pinhole, which is placed conjugate to the focal plane of the system. The confocal pinhole is used to limit light reaching the detector to that originating from the plane of focus.

(iii) Wavefront sensing: Wavefront sensing takes place in the detection arm of the instrument. The wavefront sensor measures the optical defects of the eye in the plane of the entrance pupil.

(iv) Wavefront compensation: Wavefront compensation is done with adaptive optics such as a deformable mirror. The shape of the deformable mirror is set to exactly compensate the distortions in the light that are caused by the aberrations of the eye.

(v) Raster scanning: Raster scanning is used to move the focused spot across the retina in a raster pattern. The extent of the pattern defines the area of the retina that is being imaged. Positional outputs from the scanning mirrors, combined with scattered intensity information from the light detector, are used to reconstruct the retinal image. Setting the sweep angle on the scanning mirrors controls the field size of the image.

During operation of the embodiment just described, light is being scanned in a raster pattern across the retina. The input light beam is stationary from light delivery through the deformable mirror and up to the first scanning mirror. The horizontal scanning mirror adds a horizontal sweeping motion to the beam. The second scanning mirror adds a vertical sweep to the beam. Both sweeping motions are done in planes that are optically conjugate to the pupil of the eye so that the beam at the plane of the pupil is stationary but it still makes a raster pattern on the retina. This property is accomplished by using relay optics between each beam-altering element in the system. According to the law of reversibility of light, the scattered light from the focused spot on the retina returns along the same path that the light traveled to generate the spot. In other words, the scattered light follows the scanning beam but in the opposite direction. The scattered light also gets descanned after passing through the same raster scanning mirrors. By the time the returning light has passed the horizontal scanning mirror, the beam is again stationary. Aberrations in the scattered light are compensated by the deformable mirror and are bounced off a beam splitter into the light detection and wavefront sensing path of the AOSLO. Having a stationary beam in the light detection arm allows the scattered light to be focused through a fixed confocal pinhole, which gives the SLO its optical sectioning capability.

Light is scanned over the retina in a raster pattern while the beam remains stationary in the plane of the pupil. After scattering, the optics of the SLO descan the beam and image the pupil of the eye onto the lenslet array of the Hartmann-Shack wavefront sensor, or the corresponding element of another wavefront sensor, e.g., a scanning wavefront sensor. The pupil is conjugate to the lenslet array, which means that the aberrations are measured in the pupil plane of the eye. The focused spots in the Hartmann-Shack wavefront sensor image are also stationary because the beam has been descanned. An image of the focused spot array in the Hartmann-Shack sensor is obtained by taking a time exposure of the focused spots with a CCD array detector. These spot images are analyzed to determine the aberrations of the eye being measured. In a typical Hartmann-Shack wavefront measurement, the aberrations are measured for light originating from a stationary focused spot on the retina. In high-speed ophthalmic Hartmann-Shack applications, a system that employs a linear scanning spot has been developed. In this implementation, the source of the light on the retina is constantly moving in a raster during the time exposure, and the Hartmann-Shack sensor measures the average wavefront aberration over the entire field of the image. The aberration over the image field is expected to change slightly because aberrations change with off-axis object position. Nonetheless, these changes are small since it has been demonstrated that the eye is nearly isoplanatic over a one-degree field. Therefore, the use of a scanning beam as the source does not present a disadvantage to the measurement, but rather it presents several unique advantages, which are listed below:

1) By using the same light source for wavefront sensing and imaging, the optics are simplified (no additional light source is necessary for wavefront sensing), and no correction has to be made for the chromatic aberration of the eye between the wavefront sensing and imaging wavelengths.

2) Wavefront sensing is always done on the same retinal region as the images that are taken, since the source of the wavefront measurement is also the imaging light.

3) Measuring and compensating the average wavefront over the entire image field will result in a more uniform correction for aberrations, which will result in better image quality over the field.

4) Wavefront measurements are not affected by noise due to laser speckle since the time-averaged image of a moving spot on the retina despeckles the image. This advantage has already been applied to wavefront sensing but not to its application for SLO.

5) The wavefront-sensing configuration described here is easily adaptable to real-time wavefront sensing and compensation. This advantage stems from the fact that the wavefront sensing signal is always present during imaging since imaging and wavefront sensing use the same light source.

6) The optical path to the wavefront sensor is the same as to the photomultiplier, with the exception of three aberration-corrected achromatic lenses (two in the wavefront sensor path and one in the photomultiplier path). The aberrations that are measured in the wavefront sensor will be the same as the aberrations of the light reaching the confocal pinhole, which reduces the non-common path errors.

In at least one embodiment, the wavefront compensation is done with a deformable mirror (DM) placed conjugate to the pupil in the stationary part of the optical path, prior to the raster scanning mirrors. Having the DM in this part of the path means that the mirrors that are used to focus the pupil image onto the DM can be as small as the maximum beam diameter and do not have to be enlarged to enclose the maximum scan angle. This reduces the size and cost of the instrument and maintains better image quality in the optics of the instrument.

By using AO in a SLO, the lateral resolution of retinal images is expected to improve by up to three times. This has already been demonstrated in conventional ophthalmoscopes equipped with AO. The main advantage of applying AO in a SLO will be the improvements in axial resolution. The axial resolution may be improved by up to 10 times over conventional SLO's.

Equivalent Technologies: Successful implementation of AO in a SLO does not rely on the specific technologies described in this disclosure. The following two paragraphs describe equivalent AO technologies that can be implemented with the same advantages.

Any wavefront sensing technology can be employed that is based on objective measurement and does not rely on coherent light to perform the wavefront measurement. Alternative techniques include but are not limited to laser ray tracing techniques, Tscherning aberroscopic techniques and crossed-cylinder aberrometer techniques.

Any wavefront compensation technique can be employed that does not rely on the use of coherent light. Alternative methods for wavefront sensing include, but are not limited to, liquid crystal spatial light modulators, micro-electro-machined (MEMs) membrane mirrors, MEMs segmented mirrors, bimorph deformable mirrors and electrostatic membrane deformable mirrors.

One set of applications involves the direct imaging applications that will benefit from high-resolution images. Such applications include the early diagnosis of retinal disorders like diabetic retinopathy, retinitis pigmentosa, age-related macular degeneration, or glaucoma. Other applications will be to visualize structures in the retina such as the nerve fibers, cone and rod photoreceptors, single capillaries in the retina and choroid, and retinal pigmented epithelium cells. High-resolution imaging will help retinal surgeons maintain a sharper image of the retina during retinal surgery.

Another set of applications are those whereby the SLO is used to image the retina at 30 frames per second and is used to observe directly the flow of single white blood cells.

Another set of applications are those where stimuli or treatment lasers are projected directly onto the retina as part of the raster scan. These applications include photodynamic therapy, laser microphotocoagulation, microperimetry of the retina, and eye tracking.

The SLO can use a confocal pinhole to suppress light from outside of the focal plane, which gives the SLO its optical slicing capability. This property of the SLO can be improved by implementing AO to measure and correct the aberrations of the eye. By reducing the aberrations of the eye through AO compensation, both axial and lateral resolution can be improved.

BRIEF DESCRIPTION OF THE DRAWINGS

A preferred embodiment of the present invention and variations thereof will be disclosed in detail with reference to the drawings, in which.

DETAILED DESCRIPTION OF THE PREFERRED EMBODIMENTS

Figure 1:
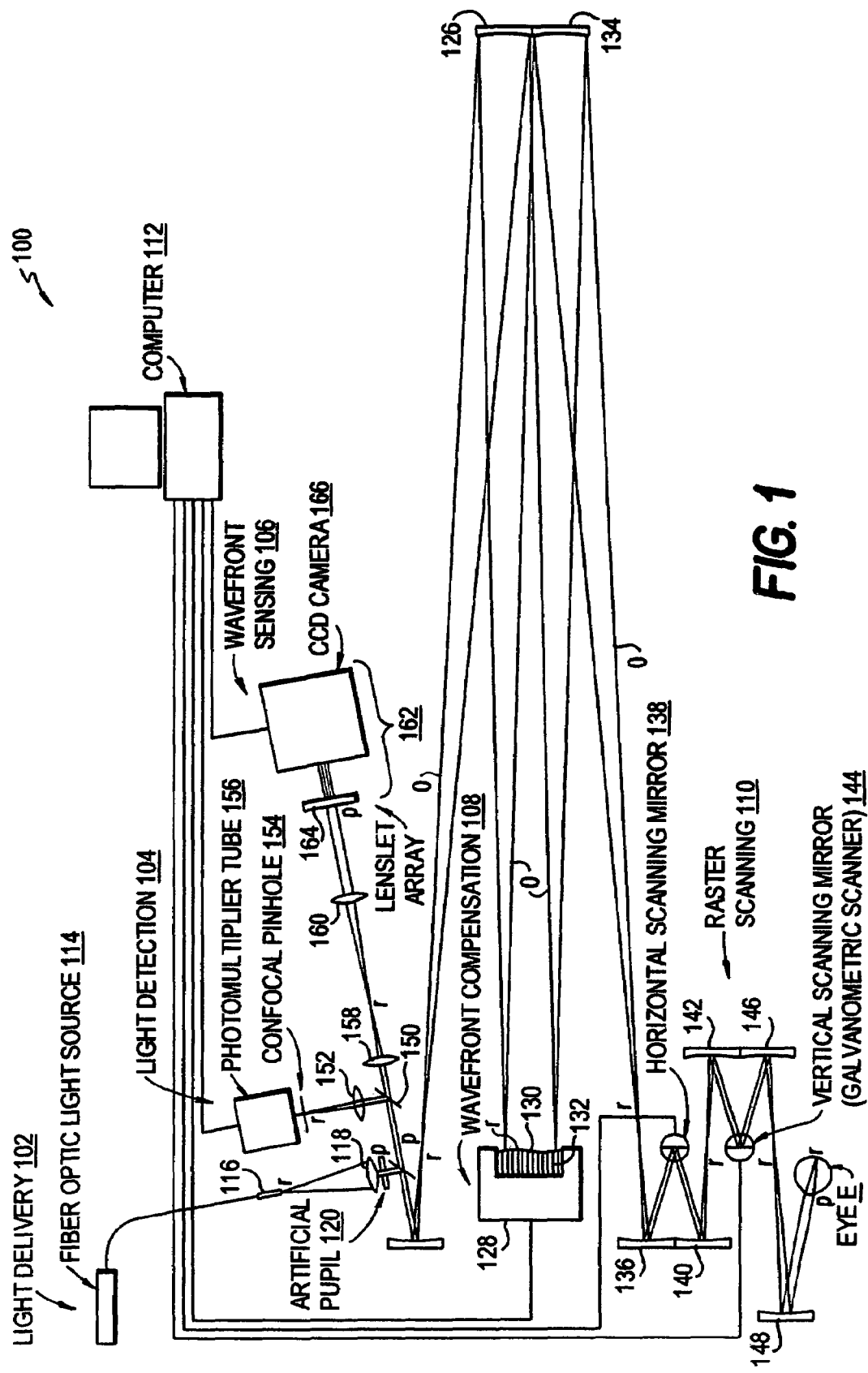
FIG. 1 is a schematic diagram of a scanning laser ophthalmoscope incorporating adaptive optics.

A preferred embodiment of the present invention and variations thereof will now be set forth in detail with reference to the drawings, in which like reference numerals refer to like elements or operational steps throughout.

FIG. 1 shows a schematic diagram of the scanning laser ophthalmoscope using adaptive optics (AOSLO). In FIG. 1, points on the optical path which are conjugate to the pupil of the eye are labeled p, while points on the path that are conjugate to the retina are labeled r.

As mentioned above, the AOSLO 100 includes a light delivery section 102, a light detection section 104, a wavefront sensing section 106, a wavefront compensation section 108 and a raster scanning section 110. All five sections are under the control of a computer 112.

In the light delivery section 102, light from a fiber optic light source 114 is expanded by a beam expander 116 and collimated by a collimating lens 118. The collimated light is made incident on an artificial pupil 120 to produce a smaller beam of light, which is injected into the common optical path O of the AOSLO 100 by a 5% reflecting beam splitter 122.

Once in the optical path O, the light is reflected by spherical mirrors 124 and 126 to the wavefront compensation section 108. Mirrors are used both to fold the optical path, thereby making the system more compact, and to avoid the problems of chromatic aberration and back reflection that affect lenses. The wavefront compensation section 108 includes a deformable mirror 128. As known in the art, the deformable mirror 128 includes a deformable mirror surface 130 deformed by multiple actuators (e.g., piezoelectric actuators) 132. An example of a deformable mirror is the 37-channel deformable mirror produced by Xinetics, Andover, Mass. The deformable mirror 128 is placed in the common optical path O conjugate to the entrance pupil of the eye E. Under the control of the computer 112, the actuators 132 deform the mirror surface 130 to compensate for wavefront aberrations in a manner that will be described in detail below.

Light reflected from the mirror surface 132 is reflected to a spherical mirror 134 and thence to the raster scanning section 110. In the raster scanning section 110, the light is reflected via a spherical mirror 136 to a horizontal scanning mirror 138, which is implemented as a resonant scanner under control of the computer 112. The light horizontally scanned by the horizontal scanning mirror 138 is reflected via two spherical mirrors 140 and 142 to a vertical scanning mirror 144, which is implemented as a galvanometric scanner under control of the computer 112. A resonant scanner-galvanometric scanner combination produced by Electro-Optics Products Corp., Flushing Meadows, N.Y., can be used. The light which has been both horizontally and vertically scanned is reflected via spherical mirrors 146 and 148 to the retina of the eye E. The light is scanned across an area of the retina whose extent is determined by the horizontal and vertical scanning extents of the scanning mirrors 138 and 144, which in turn are controlled by the computer 112.

Light reflected from the retina of the eye E travels back along the common optical path O, in which it is descanned by the scanning mirrors 144 and 138, to a beam splitter 150 to be split between the light detection section 104 and the wavefront sensing section 106. The beam splitter 150 can be implemented as a partially reflecting mirror, although an active beam splitter will be described in detail below.

The portion of the light diverted to the light detection section 104 is focused by a lens 152 onto a confocal pinhole 154 which is in a plane conjugate to the retina. Light passing through the confocal pinhole 154 is imaged by a photomultiplier tube 156 to produce signals which can be converted into an image by the computer 112. The hardware used can be a GaAs photomultiplier tube from Hamamatsu, Japan, and a GenesisLC frame grabbing board from Matrox, Montreal, Quebec, Canada.

The portion of the light passed to the wavefront sensing section 106 is collimated by lenses 158 and 160 and is passed to a Hartmann-Shack detector 162. As known in the art, the Hartmann-Shack detector 162 includes a lenslet array 164 which breaks up the light into an array of spots and a CCD camera or other suitable imaging device 166 which images the spots. The deviation of each spot from the position which it would occupy in the absence of wavefront aberrations allows a determination of those aberrations in the computer 112. Techniques for determining the aberrations up to the tenth Zernike order are known in the art. The computer 112 uses those aberrations to control the deformable mirror 128 to compensate for those aberrations.

A drawback of using mirrors is that astigmatism and other aberrations are introduced when they are off axis. To overcome that drawback, a cylindrical correction can be placed in the spectacle plane of the eye, and optical design software such as ZEMAX, published by Focus Software, Tucson, Ariz., can be used to minimize the remaining high-order system aberrations through optimal placement of the mirrors. Off-the-shelf spherical reflecting mirrors can be used.

Figure 2:
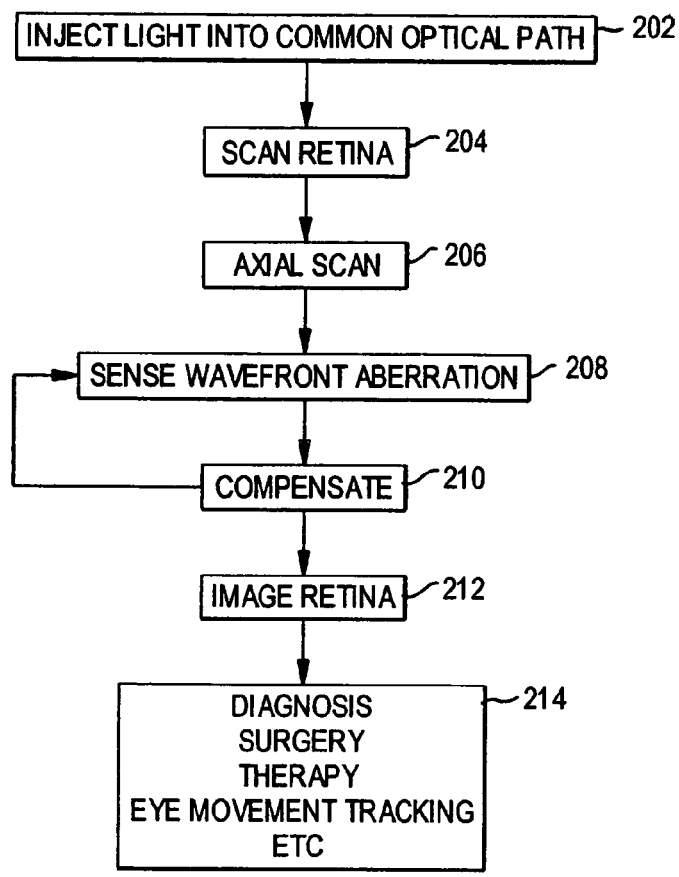
FIG. 2 is a flow chart of operational steps carried out with the ophthalmoscope of FIG. 1.

The AOSLO 100 operates as shown in the flow chart of FIG. 2. In step 202, the light delivery section 102 injects light into the common optical path O. In step 204, the scanning section 110 scans the retina. In an optional step 206, the retina can be axially scanned, in a manner to be described below, to produce a three-dimensional image.

In step 208, the wavefront sensing section 106 senses the wavefront aberrations. In step 210, the wavefront compensation section 108 compensates for those aberrations. Steps 208 and 210 can be performed iteratively.

In step 212, the light detection section 104 images the retina. In step 214, the image of the retina is used for any desired purpose, including diagnosis of the retinal condition, surgery on the retina, application of therapeutic laser light to the retina, or eye movement tracking, as will be explained in detail below.

Figure 3:
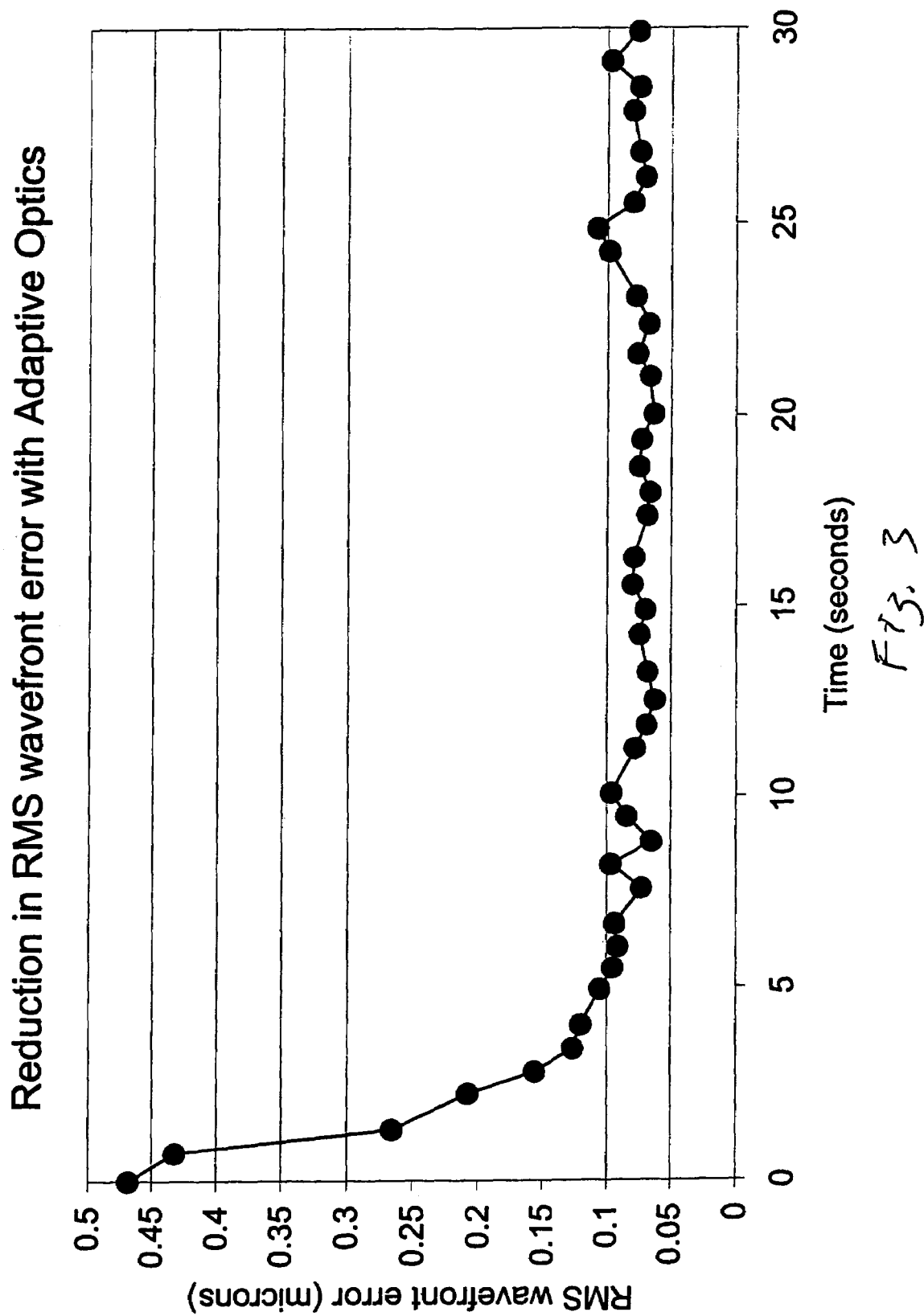
FIG. 3 is a graph of detected wavefront aberrations for multiple iterations of wavefront sensing and compensation.

As just noted, the steps of sensing and compensating the wavefront aberrations can be performed iteratively. FIG. 3 shows the results of such iterations for a 6.3 mm pupil in a living human eye. The x-axis is the time in seconds over which the correction took place. Each point represents the root mean square aberration after a single iteration. The magnitude of aberrations, measured up to the tenth order in this case, is reduced sixfold for the 6.3 mm pupil.

Figure 4:
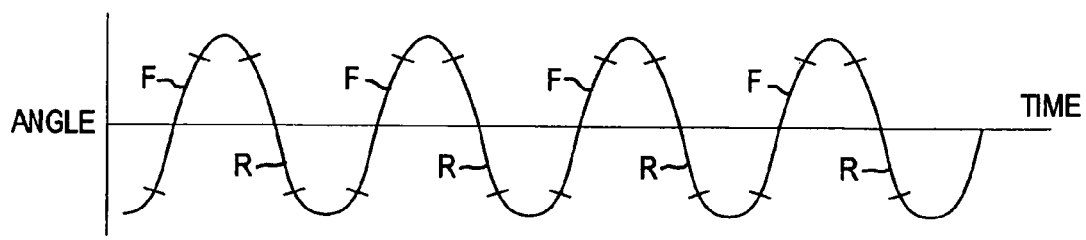
FIG. 4 is a graph of a horizontal angular position of a scanning line on the retina.

A specific embodiment of the beam splitter 150 and its operation, namely, the timeshare embodiment, will be described. FIG. 4 shows a graph of the horizontal angular position of the horizontally scanned line on the retina as a function of time. As shown, the position is a sinusoidal function of time, which has roughly linear sections. During the linear section of each forward scan F, the scattered light is detected by the light detection section 104 to image one line in a frame in which the retina is imaged. During the linear section of each reverse scan R, the scattered light is passed to the wavefront sensing section 106 to measure the wavefront aberration.

Figure 5A:
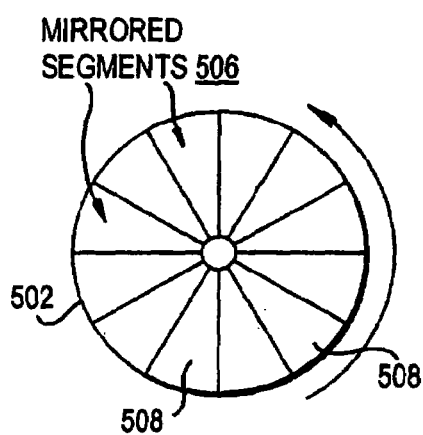
FIGS. 5A and 5B are schematic diagrams of a time-share beam splitter usable in the ophthalmoscope of FIG. 1.
Figure 5B:
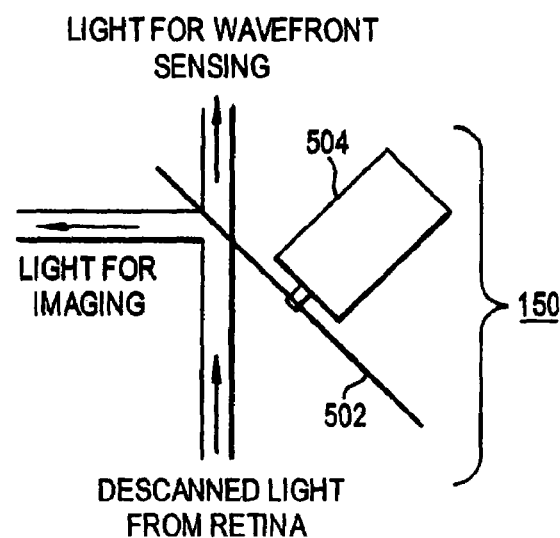

The structure of the beam splitter 150 is shown in FIGS. 5A and 5B. The beam splitter 150 includes a disk 502 rotated by a motor 504. The disk 502 has mirrored segments 506 alternating with non-mirrored segments 508, so that the light is alternately reflected to the light detection section 104 and passed to the wavefront sensing section 106.

The reverse direction R of the scan can be used for wavefront sensing by splitting the light between the wavefront sensor and the photomultiplier tube with the segmented mirror that alternates between transmitting the light to the wavefront sensor and reflecting the beam toward the photomultiplier tube. The timing of the mirror is phase-locked to the horizontal scan frequency. The light reaching the wavefront sensor can be integrated for any desired period of time independently of the scan rate or the frame rate of a typical AOSLO. The aberrations of the eye change dynamically and so the image quality will be better if the eye's aberrations are measured and compensated while the retina is imaged.

The deformable mirror can be used as an axial scanning element in axial sectioning. Axial sectioning requires an optical correction to change the depth plane of the focused raster scan on the retina. The use of the deformable mirror presents some unique advantages, which include reducing the number of moving parts in the system, and increasing its speed and precision. The thickness of the retina is about 300 microns. A focal change of less than 1 diopter is sufficient to change the focal plane by this amount.

The present method can be implemented with the deformable mirror described in the current design or it can be done with alternate, dynamic wavefront compensation techniques, such as micro-electrical machined (MEMs) deformable mirrors, or membrane mirrors.

Wavefront sensing and correction can be done simultaneously with axial sectioning, in a technique called "non-null wavefront compensation." The optical path for wavefront sensing is not confocal, so light is detected from all scattered layers in the retina simultaneously. Therefore, when the aberrations of the eye are corrected, the defocus is also adjusted to put the focal plane into the mean location of all the scattering layers in the retina. If wavefront sensing and compensation were to be done simultaneously with axial sectioning, the mirror would continually try to adjust its defocus to move the image plane back to the mean location of the scattering surfaces. Such a correction would defeat attempts to change the focal plane of the system and image different layers of the retina. This is overcome in the following way. Rather than letting the AO system converge to a null state (i.e., zero aberrations), the AO system is programmed to converge to a finite defocused state. By converging to a defocused state, the AO system will adjust the focal plane, while still correcting all other aberrations to zero. This technique will allow the operator to change the focal plane while still having the benefit of simultaneous wavefront sensing and compensation.

The AOSLO described herein permits the direct imaging of features in the living retina that have never been observed, features that include retinal pigment epithelium cells, individual nerve fibers, cone and rod photoreceptors, single capillaries in the retina and choroid and white blood cells. With the improvements in axial sectioning, it will be possible to generate the first microscopic scale three-dimensional images of living human retina at high resolutions.

The AOSLO can be used for the diagnosis of retinal disorders like diabetic retinopathy, retinitis pigmentosa, age-related macular degeneration, or glaucoma.

In still another use, high-resolution images of the retina will permit highly accurate measurements of eye movements needed for surgical applications or applications requiring eye tracking.

In yet another use, stimuli or treatment lasers are projected directly onto the retina as part of the raster scan. Treatments include photodynamic therapy, laser microphotocoagulation, and microperimetry of the retina.

Images have been collected from the eyes of five persons ranging in age from the $2^{nd}$ to $7^{th}$ decade. The RMS wavefront error after AO compensation ranged from 0.05 to 0.15 µm over a 6.3 mm pupil. The patients used a dental impression mount fixed to an X-Y-Z translation stage to set and maintain eye alignment during the wavefront correction and imaging. The retinal location of the wavefront correction and imaging was controlled by having each patient view a fixation target. A drop of 1% tropicamide was instilled to dilate the pupil and to minimize accommodation fluctuations.

Experimental data will now be set forth. The correction of aberrations provided by the present invention permits retinal imaging of high quality, as will be seen.

Figures 6A, 6B:
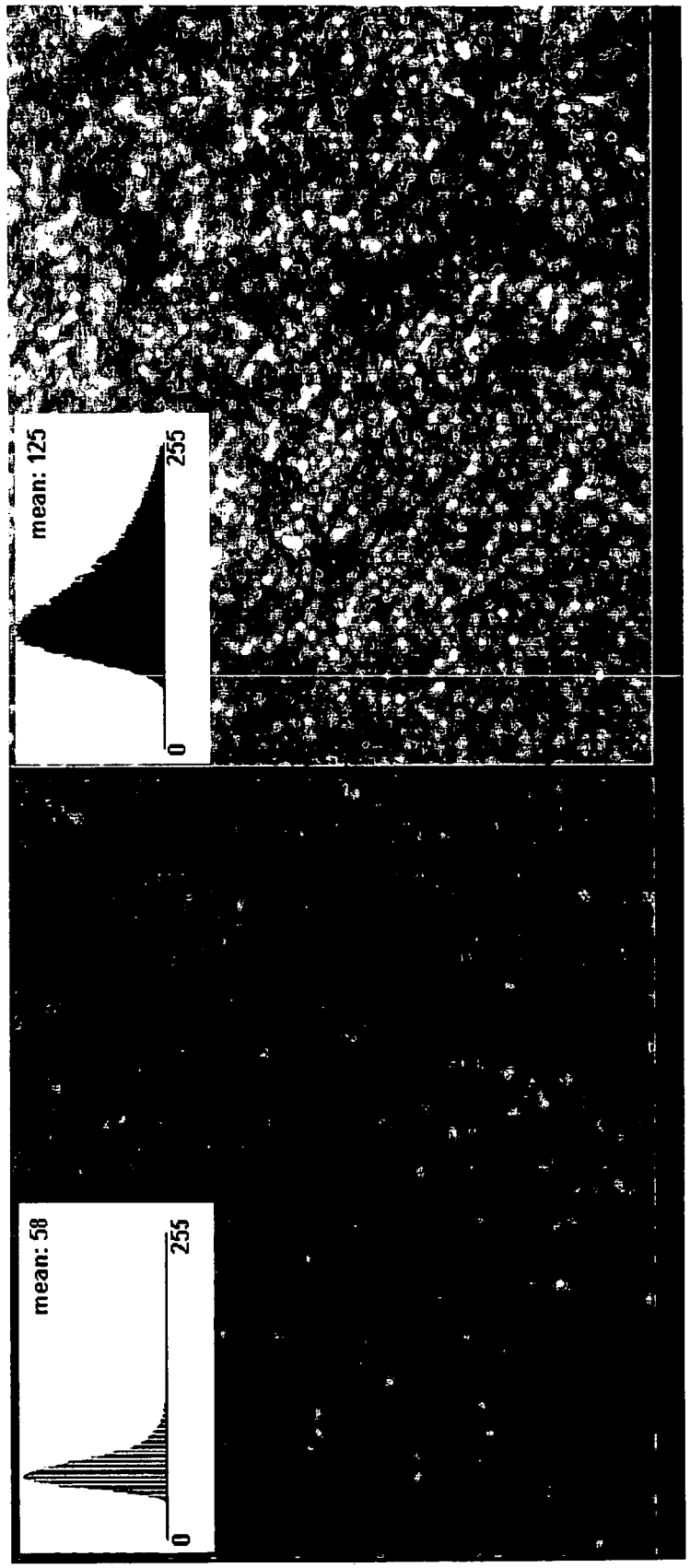
FIGS. 6A and 6B show images of a retina taken without and with aberration correction, respectively.

FIGS. 6A and 6B show the same area of the retina of one patient taken without (FIG. 6A) and with (FIG. 6B) aberration correction. The RMS wavefront error was reduced from 0.55 to 0.15 µm. Another advantage was that correction of the aberrations caused more light to be focused through the confocal pinhole, thus increasing the amount of light for imaging. The inset in each of FIGS. 6A and 6B shows a histogram of gray scales in the image.

Figure 7A:
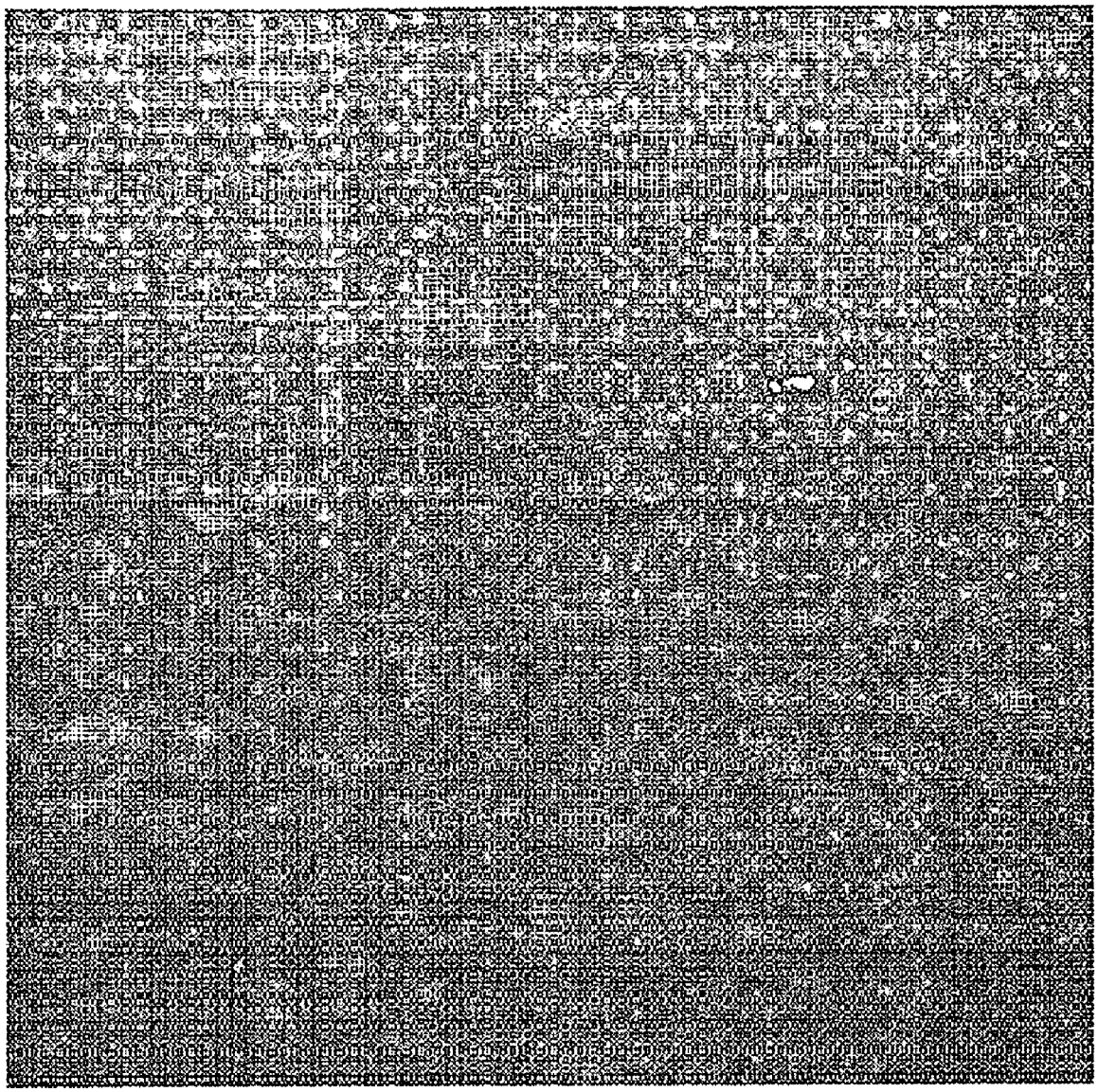
FIGS. 7A–7C show images taken of different axial sections of a retina.
Figure 7B:
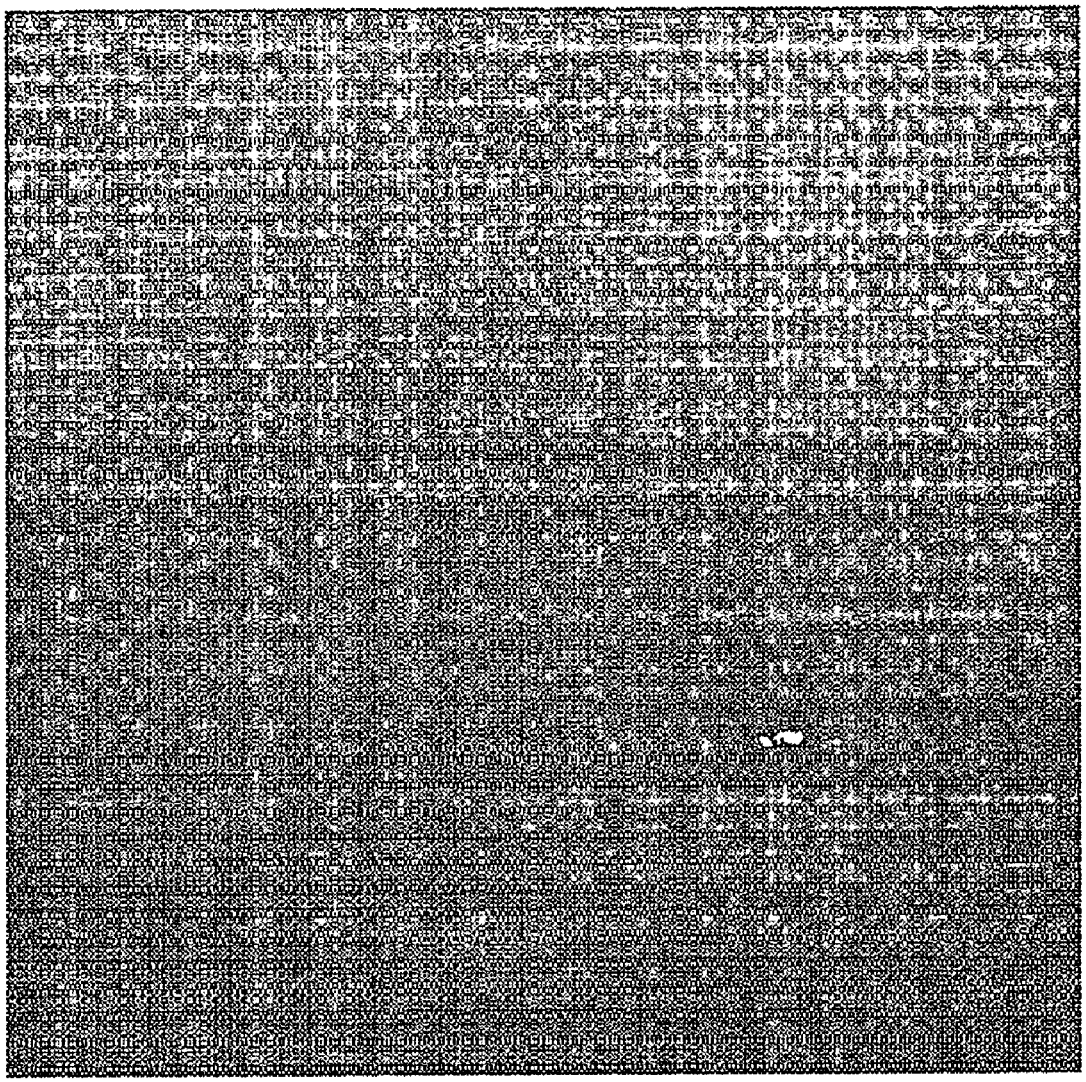
Figure 7C:
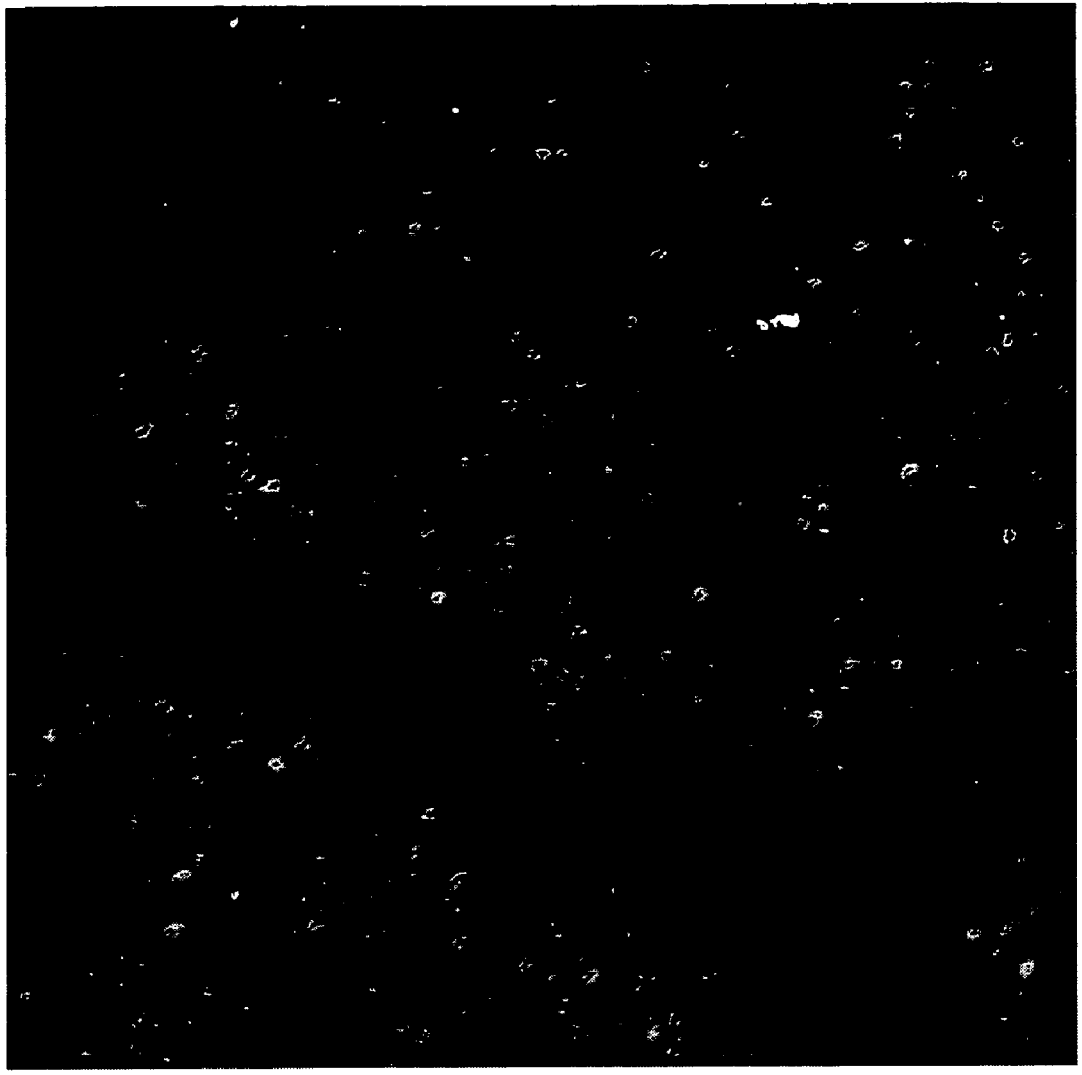

FIGS. 7A–7C show axial sectioning of the retina, which is possible because of the reduction in aberrations. The images are from a location 4.5 degrees superior to the fovea. In FIG. 7A, the focal plane is at the surface of the nerve fibers. FIG. 7B shows a slightly deeper optical section in which less nerve fiber is seen but the blood vessel is in focus. FIG. 7C shows an image in which the focal plane is at the level of the photoreceptors, which are about 300 µm deeper than the image of FIG. 7A.

Figure 8:
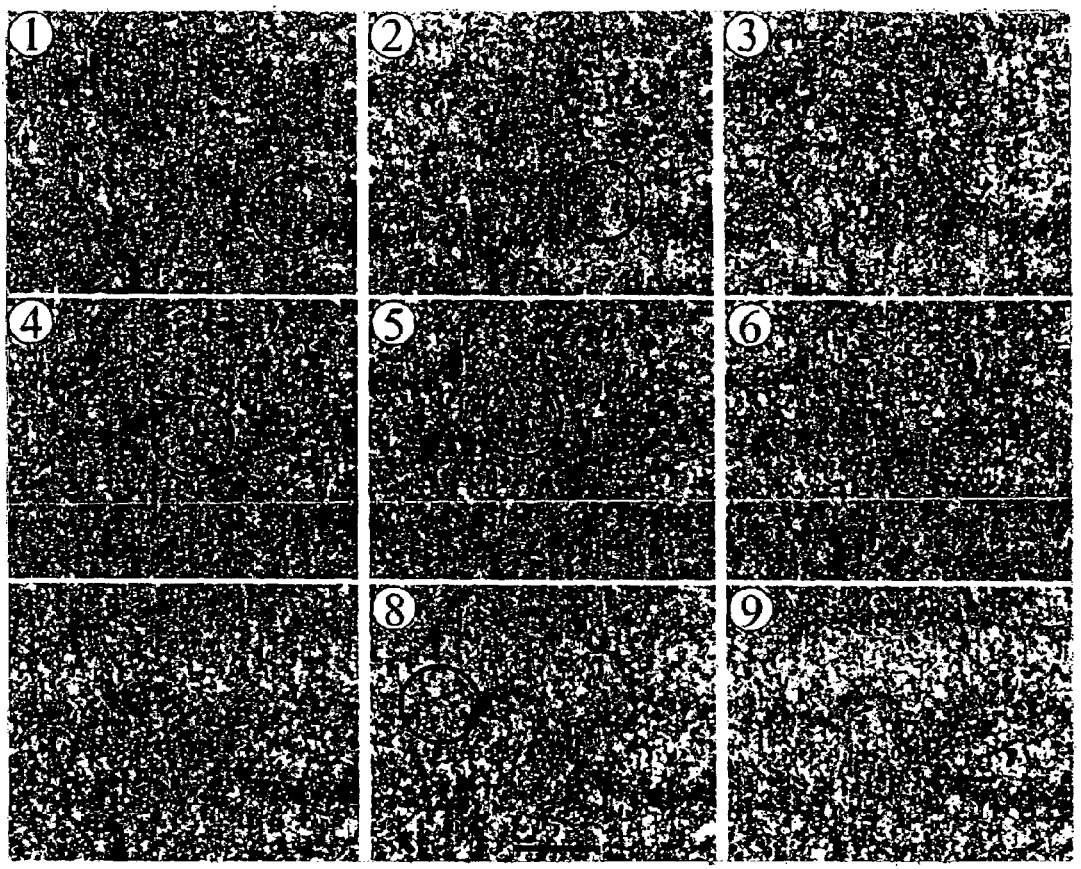
FIG. 8 shows a video image sequence in which a blood cell is moving through a retinal capillary.

FIG. 8 shows a sequence of video frames in which the passage of a white blood cell through the smallest retinal capillaries is directly observed in a living human eye. The scale bar at the bottom is 100 microns.

Figure 9:
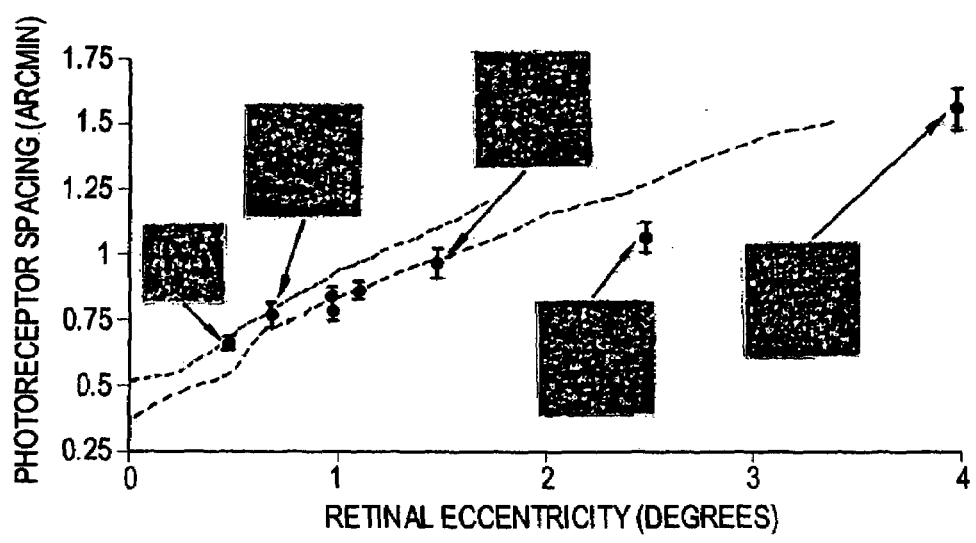
FIG. 9 shows images of cone cells taken at various locations on a retina and calculations of their spacing.

FIG. 9 shows images of cone photoreceptors resolved at retinal locations from 0.5 to 4 degrees from the fovea. The long-dashed line shows data from Curcio et al, "Human photoreceptor topography," *J. Comp. Neurol.* 1990; 292: 497–523, while the short-dashed line shows psychophysical estimations of cone spacing from D. Williams, "Topography of the foveal cone mosaic in the living human eye," *Vision Res.* 28, 433–454 (1988).

Preliminary estimates of the resolution of the present invention are about 2.5 µm lateral and about 100 µm axial. By contrast, conventional SLO's have a typical resolution of 5 µm lateral and 300 µm axial.

The AOSLO of the preferred embodiment operates at a frame rate of 30 Hz, which permits visualization of blood flow in the retinal capillaries. Also, the real-time imaging provides feedback on image quality and image location. Further, axial sectioning can be implemented. Conventional flood-illumination imaging, even with AO, cannot offer such advantages.

The following article concerning the present invention is hereby incorporated by reference in its entirety into the present disclosure: A. Roorda et al, "Adaptive optics scanning laser ophthalmoscopy," *Optics Express*, Vol. 10, No. 9, May 6, 2002, pp. 405–412.

While a preferred embodiment of the present invention and variations thereon have been disclosed above, those skilled in the art who have reviewed the present disclosure will readily appreciate that other embodiments can be realized within the scope of the invention. For example, numerical values are illustrative rather than limiting. Also, variations on the configuration of the common optical path are possible, and variations on the hardware have been noted above. Further, while the present invention has been disclosed with regard to human subjects, veterinary applications are also possible. Therefore, the present invention should be construed as limited only by the appended claims.

What is claimed is:

1. A method of imaging an area of a retina of a living eye, the method comprising:
   (a) providing light from a light source;
   (b) injecting the light from the light source into a common optical path;
   (c) performing a two-dimensional transverse scan of a focused spot of the light from the light source on the area of the retina such that the light is stationary at a pupil plane of the living eye;
   (d) receiving light reflected from the focused spot on the retina back into the common optical path;
   (e) from a first portion of the light reflected from the retina, detecting a wavefront aberration of the eye;
   (f) disposing an adaptive optical element in the common optical path between the light source and the eye;
   (g) controlling the adaptive optical element to compensate for the wavefront aberration in the light scanned on the area of the retina to project the focused spot onto the retina;
   (h) controlling the adaptive optical element to compensate for the wavefront aberration in the light reflected from the focused spot on the retina back into the common optical path; and
   (i) from a second portion of the light reflected from the retina, producing an image of the area of the retina.

2. The method of claim 1, wherein step (d) comprises descanning the light reflected from the retina.

3. The method of claim 1, wherein the adaptive optical element comprises a deformable mirror.

4. The method of claim 1, wherein step (c) comprises raster scanning a light spot on the retina.

5. The method of claim 4, wherein the raster scanning is performed with at least one scanning mirror.

6. The method of claim 5, wherein step (c) further comprises controlling a sweep angle of the at least one scanning mirror to control a size of an area on the retina which is scanned.

7. The method of claim 1, wherein step (e) is performed with a Hartmann-Shack detector.

8. The method of claim 7, wherein:
step (i) is performed with a photodetector; and
the method further comprises providing a beam splitter in the common optical path to split the light reflected from the retina between the Hartmann-Shack detector and the photodetector.

9. The method of claim 8, wherein the beam splitter comprises a rotating mirror having mirrored segments and transparent segments for time division of the light reflected from the retina.

10. The method of claim 9, wherein a period of the time division equals a period of the scanning of step (c).

11. The method of claim 1, wherein steps (e) and (g) are performed iteratively.

12. The method of claim 1, wherein steps (e) and (i) are performed concurrently.

13. The method of claim 1, further comprising (j) controlling the adaptive optical element for axial sectioning.

14. The method of claim 13, wherein step (g) comprises correcting the focus to a non-null state.

15. The method of claim 13, wherein step (i) comprises producing a three-dimensional image of the retina.

16. The method of claim 1, further comprising using the image to diagnose a disorder of the retina.

17. The method of claim 1, further comprising using the image to track movement of the eye.

18. The method of claim 1, wherein step (c) comprises projecting a stimulus or treatment to the retina.

19. The method of claim 1, wherein step (i) is performed a plurality of times to form a sequence of said images, and further comprising using the sequence of said images to measure a flow of blood cells in at least one capillary of the retina.

20. The method of claim 1, wherein step (i) is performed with a confocal pinhole and a photodetector.

21. A system for imaging an area of a retina of a living eye, the system comprising:
a light delivery section, comprising a light source, for providing light from the light source and for injecting the light from the light source into a common optical path;
a scanning section for performing a transverse two-dimensional scan of a focused spot of the light from the light source on the area of the retina light is stationary at a pupil plane of the living eye and such that light reflected from the focused spot on the retina is received back into the common optical path;
a wavefront sensing section, receiving a first portion of the light reflected from the retina, for detecting a wavefront aberration of the eye;
a wavefront compensation section, comprising an adaptive optical element disposed in the common optical path between the light source and the eye, for compensating for the wavefront aberration in the scanned on the area of the retina to project the focused spot onto the retina and for compensating for the wavefront aberration in the light reflected from the focused spot on the retina back into the common optical path; and
a light detection section, receiving a second portion of the light reflected from the retina, for producing an image of the area of the retina.

22. The system of claim 21, wherein the scanning section descans the light reflected from the retina.

23. The system of claim 21, wherein the adaptive optical element comprises a deformable mirror.

24. The system of claim 21, wherein the scanning section comprises a device for raster scanning a light spot on the retina.

25. The system of claim 24, wherein the device for raster scanning comprises at least one scanning mirror.

26. The system of claim 21, wherein the wavefront sensing section comprises a Hartmann-Shack detector.

27. The system of claim 26, wherein:
the light detection section comprises a photodetector; and
the system further comprises a beam splitter in the common optical path for splitting the light reflected from the retina between the Hartmann-Shack detector and the photodetector.

28. The system of claim 27, wherein the beam splitter comprises a rotating mirror having mirrored segments and transparent segments for time division of the light reflected from the retina.

29. The system of claim 21, wherein the light detection section comprises a confocal pinhole.

30. The method of claim 14, wherein steps (e) and (g) are performed iteratively to correct the focus to the non-null state.

* * * * *

UNITED STATES PATENT AND TRADEMARK OFFICE
CERTIFICATE OF CORRECTION

| | |
|---|---|
| PATENT NO. | : 7,118,216 B2 |
| APPLICATION NO. | : 11/125331 |
| DATED | : October 10, 2006 |
| INVENTOR(S) | : Austin Roorda |

Page 1 of 1

It is certified that error appears in the above-identified patent and that said Letters Patent is hereby corrected as shown below:

In the Claims:

In Claim Number 21, at Col. 12, Line 3, after the word "retina" insert the words --such that the-- and line 13, before the word "scanned" insert the word --light--

Signed and Sealed this

Fifth Day of October, 2010

David J. Kappos
*Director of the United States Patent and Trademark Office*